United States Patent
Ito et al.

(10) Patent No.: US 8,084,608 B2
(45) Date of Patent: Dec. 27, 2011

(54) 2,2'-BIPYRIDINE DERIVATIVE HAVING A REACTIVE SILYL GROUP, ITS PRODUCTION METHOD, AND TRANSITION METAL COMPLEX

(75) Inventors: Yusuke Ito, Joetsu (JP); Ayumu Kiyomori, Joetsu (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 149 days.

(21) Appl. No.: 12/472,615

(22) Filed: May 27, 2009

(65) Prior Publication Data

US 2009/0299068 A1 Dec. 3, 2009

(30) Foreign Application Priority Data

May 29, 2008 (JP) .................. 2008-140803

(51) Int. Cl.
*C07F 7/02* (2006.01)
*C07F 15/00* (2006.01)

(52) U.S. Cl. ............................. 546/14; 546/4

(58) Field of Classification Search .............. None
See application file for complete search history.

(56) References Cited

U.S. PATENT DOCUMENTS

| | | | |
|---|---|---|---|
| 5,463,057 A | 10/1995 | Graetzel et al. | |
| 6,288,229 B1 | 9/2001 | Komatsuzaki et al. | |
| 2008/0166712 A1 | 7/2008 | Murayama et al. | |
| 2010/0184978 A1 * | 7/2010 | Asaumi et al. | 544/296 |

FOREIGN PATENT DOCUMENTS

| | | |
|---|---|---|
| JP | 6-247880 A | 9/1994 |
| JP | 9-234374 A | 9/1997 |
| JP | 2001-64641 A | 3/2001 |
| JP | 2007-304091 A | 11/2007 |
| WO | 94/04497 A1 | 3/1994 |
| WO | WO 2008/156196 A1 * | 12/2008 |

OTHER PUBLICATIONS

Takahashi et al., Chelation-assisted electrocyclic reactions of 3-alkenyl-2,2'-bipyridines. An efficient method for the synthesis of 5,6-dihydro-1,10-phenanthroline and 1,10-phenanthroline derivatives, 5 Chem. COMMC'NS 609-611 (2008).*

T. Nishimura et al., "Ruthenium(II)-Bipyridine Anchored Montmorillonite-Catalyzed Oxidation of Aromatic Alkenes with tert-Butyl Hydroperoxide", Tetrahedron Letters, 1998, pp. 4359-4362, vol. 39.

European Search Report dated Sep. 16, 2009, issued in corresponding European Patent Application No. 09251436.3.

Stange, A. F. et al., "Ruthenium and rhenium complexes with silyl-substituted bipyridyl ligands"; Journal of Organometallic Chemistry, 2000, vol. 612, pp. 117-124, XP002544250.

* cited by examiner

*Primary Examiner* — Janet Andres
*Assistant Examiner* — Timothy R Rozof
(74) *Attorney, Agent, or Firm* — Westerman, Hattori, Daniels & Adrian, LLP

(57) ABSTRACT

A 2,2'-bipyridine derivative having a reactive silyl group represented by the following general formula (1):

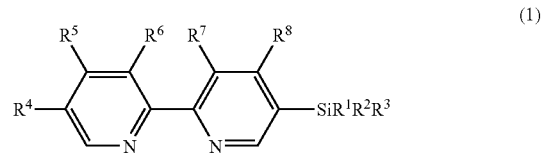

wherein $R^1$ and $R^2$ represent a substituent selected from a monovalent hydrocarbon group, an organoxy group, an acyloxy group, hydroxy group, a halogen atom, hydrogen atom, mercapto group, an amino group, cyano group, cyanate group, isocyanate group, thiocyanate group, and isothiocyanate group; $R^3$ represents a monovalent aliphatic unsaturated hydrocarbon group, an organoxy group, an alkoxy group, an acyloxy group, hydroxy group, a halogen atom, hydrogen atom, mercapto group, an amino group, cyano group, cyanate group, isocyanate group, thiocyanate group, and isothiocyanate group; $R^4$ represents a reactive silyl group represented by the formula: $R^1R^2R^3Si$, a monovalent hydrocarbon group, or hydrogen atom; $R^5$, $R^6$, $R^7$, and $R^8$ are a monovalent hydrocarbon group or hydrogen atom.

11 Claims, 1 Drawing Sheet

2,2'-BIPYRIDINE DERIVATIVE HAVING A REACTIVE SILYL GROUP, ITS PRODUCTION METHOD, AND TRANSITION METAL COMPLEX

CROSS-REFERENCE TO RELATED APPLICATION

This non-provisional application claims priority under 35 U.S.C. §119(a) on Patent Application No. 2008-140803 filed in Japan on May 29, 2008, the entire contents of which are hereby incorporated by reference.

TECHNICAL FIELD

This invention relates to a 2,2'-bipyridine derivative having a reactive silyl group which is useful as a ligand for a metal complex, its production method, and a transition metal complex produced by using the 2,2'-bipyridine derivative.

BACKGROUND OF THE INVENTION

A 2,2'-bipyridine derivative works as a chelating ligand for various type of metals, and it readily forms various metal complexes. The thus formed metal complex is useful in industry since oxidation-reduction potential, molecular orbital, and the like can be readily adjusted by introducing an adequate substituent on the bipyridine ring. Among such metal complexes, a transition metal complex having 2,2'-bipyridine derivative ligand can be used for various applications. For example, Japanese Patent Application Laid-Open No. 2007-304091 discloses a gene detection method using electrochemical activity of a ruthenium complex and an osmium complex. Japanese Patent No. 3731752 discloses that a ruthenium complex can be used for a dye sensitized solar battery, and that carboxyl group at the terminal will be immobilized on a porous membrane by forming a chemical bond with the titanium oxide particle, and absorb visible light in substantially all visible range at high conversion rate. Japanese Patent Application Laid-Open No. 2001-64641 discloses use of a ruthenium complex for a luminescent material. Japanese Patent Application Laid-Open No. 9-234374 discloses that ruthenium complex and manganese complex can be used as an oxidation catalyst, and Japanese Patent Application Laid-Open No. 6-247880 discloses that use of complexes of iron, cobalt, ruthenium, and the like as a catalyst for cyclization and dimerization of a conjugated diolefin.

More specifically, in the Examples of the Japanese Patent Application Laid-Open No. 6-247880, the reaction is allowed to proceed in a homogeneous system by using 0.5% by mole of the transition metal complex catalyst with respect to 1 mole of the reaction substrate. Since the transition metal complex is generally expensive, it would be preferable from the industrial point of view to collect the catalyst after the reaction for reuse. When the transition metal complex is used by preliminarily immobilizing the transition metal complex to an inorganic solid such as silica gel or alumina or an organic polymer, the transition metal complex can be readily separated after the reaction for its reuse. The transition metal complex can be loaded on such solid support by using a ligand having a reactive group capable of firmly bonding to the support. An example of such reactive group is silyl group, and silyl group can react with various types of substituents such as hydroxy group on the support. For example, Tetrahedron Letters, 1998, vol. 39, pp. 4359-4362 describes immobilization of ruthenium bipyridine complex on montmorillonite by using silyl group for use as an oxidation catalyst.

However, the ligand used in Tetrahedon Letters, 1998, vol. 39, pp. 4359-4362 is bipyridine substituted at position 6 with silyl group, and formation of bis(bipyridine) complex and tris(bipyridine) complex as described in Japanese Patent Application Laid-Open No. 2007-304091, Japanese Patent No. 3731752, or Japanese Patent Application Laid-Open No. 2001-64641 by using such ligand has been difficult due to steric hindrance by the substituent at the position 6. In view of such situation, development of a new ligand which enables immobilization of various transition metal complexes on the solid support has been highly awaited. In the case of the Japanese Patent No. 3731752, electronic interaction between the transition metal complex and the solid support used for immobilization is utilized. Therefore, a ligand which enables immobilization of the transition metal complex at a distance closer to the support has been desired.

SUMMARY OF THE INVENTION

The present invention has been completed in view of the situation as described above, and accordingly, an object of the present invention is to provide a 2,2'-bipyridine derivative which is useful as a ligand of a supported-type metal complex and its production method. Another object of the present invention is to provide a transition metal complex produced by using such 2,2'-bipyridine derivative and its production method.

The inventors of the present invention made an intensive study, and found a novel 2,2'-bipyridine derivative which has a reactive silyl group at position 5, its production method, and a transition metal complex produced by using such 2,2'-bipyridine derivative and its production method. The present invention has been completed on the bases of such finding.

Accordingly, the present invention provides a 2,2'-bipyridine derivative, its production method, and a transition metal complex having the 2,2'-bipyridine derivative as the ligand as described below.

[I] A 2,2'-bipyridine derivative having a reactive silyl group represented by the following general formula (1):

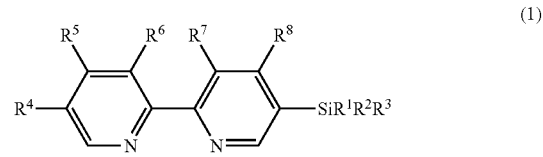

wherein $R^1$ and $R^2$ independently represent a substituent selected from an unsubstituted or substituted monovalent hydrocarbon group containing 1 to 10 carbon atoms, an unsubstituted or substituted organoxy group containing 1 to 10 carbon atoms, an unsubstituted or substituted acyloxy group containing 1 to 10 carbon atoms, hydroxy group, a halogen atom, hydrogen atom, mercapto group, an unsubstituted or substituted amino group, cyano group, cyanate group, isocyanate group, thiocyanate group, and isothiocyanate group; $R^3$ represents an unsubstituted or substituted monovalent aliphatic unsaturated hydrocarbon group containing 2 to 10 carbon atoms, an unsubstituted or substituted organoxy group containing 1 to 10 carbon atoms, an unsubstituted or substituted alkoxy group containing 1 to 10 carbon atoms, an unsubstituted or substituted acyloxy group containing 1 to 10 carbon atoms, hydroxy group, a halogen atom, hydrogen atom, mercapto group, an unsubstituted or substituted amino group, cyano group, cyanate group, isocyanate group, thiocyanate group, and isothiocyanate group; $R^4$ represents a reactive silyl group represented by the formula: $R^1R^2R^3Si$, an unsubstituted or substituted monovalent hydrocarbon group containing 1 to 10 carbon atoms, or hydrogen atom; $R^5$, $R^6$, $R^7$, and $R^8$ are independently an unsubstituted or substituted monovalent hydrocarbon group containing 1 to 10 carbon atoms or hydrogen atom.

[II] The 2,2'-bipyridine derivative having a reactive silyl group wherein $R^1$ and $R^2$ in the general formula (1) are methyl group or isopropyl group.

[III] A method of producing a 2,2'-bipyridine derivative having a reactive silyl group represented by the general formula (1) wherein $R^4$ represents an unsubstituted or substituted monovalent hydrocarbon group containing 1 to 10 carbon atoms or hydrogen atom, by reacting a 5-metallo-2,2'-bipyridine derivative produced from a 5-halo-2,2'-bipyridine derivative represented the following general formula (2):

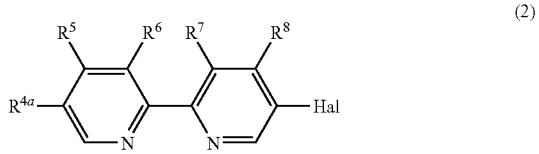

(2)

wherein Hal represents chlorine atom, bromine atom, or iodine atom, $R^{4a}$ represents an unsubstituted or substituted monovalent hydrocarbon group containing 1 to 10 carbon atoms or hydrogen atom, and $R^5$, $R^6$, $R^7$, and $R^8$ are as defined above for the formula (1), with a silicon compound represented by the following general formula (3):

$$XSiR^1R^2R^3 \quad (3)$$

wherein X represents a halogen atom or an organoxy group containing 1 to 10 carbon atoms, and $R^1$, $R^2$, and $R^3$ independently represent the same substituent as the one defined for formula (1).

[IV] A method of producing a 2,2'-bipyridine derivative having a reactive silyl group represented by the general formula (1) wherein $R^4$ represents a reactive silyl group represented by the formula: $R^1R^2R^3Si$, by reacting a 5,5'-dimetallo-2,2'-bipyridine derivative produced from a 5,5'-dihalo-2,2'-bipyridine derivative represented the following general formula (4):

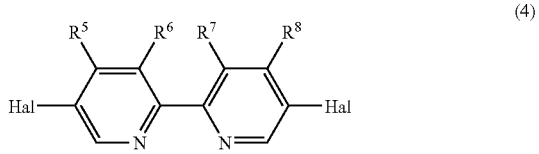

(4)

wherein Hal represents chlorine atom, bromine atom, or iodine atom, and $R^5$, $R^6$, $R^7$, and $R^8$ independently represent the same substituent as the one defined for formula (1), with a silicon compound represented by the general formula (3).

[V] A transition metal complex containing the 2,2'-bipyridine derivative having a reactive silyl group of [I] or [II] as at least one ligand.

[VI] The transition metal complex according to [V] wherein the transition metal is selected from manganese, iron, ruthenium, osmium, cobalt, rhodium, iridium, nickel, palladium, platinum, and copper.

[VII] The transition metal complex according to [V] represented by the following general formula (5):

$$(X)_mM(L^1)_n(L^2)_p \quad (5)$$

wherein M is a transition metal selected from manganese, iron, ruthenium, osmium, cobalt, rhodium, iridium, nickel, palladium, platinum, and copper, m is an integer of 0 to 3, X is independently selected from a halogen atom, thiocyanate group, thioisocyanate group, hydroxy group, cyano group, cyanate group, isocyanate group, and carbonyl group, n is an integer of 1 to 3, $L^1$ is a 2,2'-bipyridine derivative having a reactive silyl group represented by the general formula (1), p is an integer of 0 to 2, $L^2$ is a 2,2'-bipyridine derivative represented by the following general formula (6):

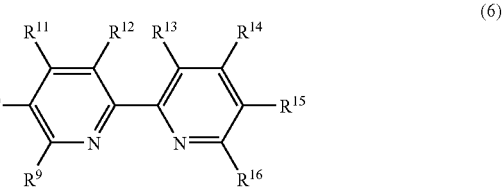

(6)

wherein $R^9$, $R^{10}$, $R^{11}$, $R^{12}$, $R^{13}$, $R^{14}$, $R^{15}$, and $R^{16}$ independently represent an unsubstituted or substituted monovalent hydrocarbon group containing 1 to 20 carbon atoms or hydrogen atom with the proviso that n+p is an integer of 1 to 3.

[VIII] A transition metal complex according to [VII] containing as its ligand a compound which is a 2,2'-bipyridine derivative having a reactive silyl group of [1] wherein $R^1$ and $R^2$ are isopropyl group.

[IX] A supported-type transition metal catalyst prepared by using the transition metal complex of any one of [V] to [VIII].

[X] A dye-sensitized photoelectric conversion device prepared by using a transition metal complex of any one of [V] to [VIII].

[XI] An electrochemical device prepared by using a transition metal complex of any one of [V] to [VIII].

[XII] A luminescent device prepared by using a transition metal complex of any one of [V] to [VIII].

The present invention provides a novel 2,2'-bipyridine derivative having a reactive silyl group and its production method. Also provided is a transition metal complex produced by using such 2,2'-bipyridine derivative and its production method. The 2,2'-bipyridine derivative is useful as the ligand of a supported-type transition metal complex.

The transition metal complex of the present invention having the 2,2'-bipyridine derivative as its ligand is also useful as a supported-type transition metal complex which can be used as a catalyst or an electrochemical device.

DETAILED DESCRIPTION OF THE INVENTION

Figure 1:
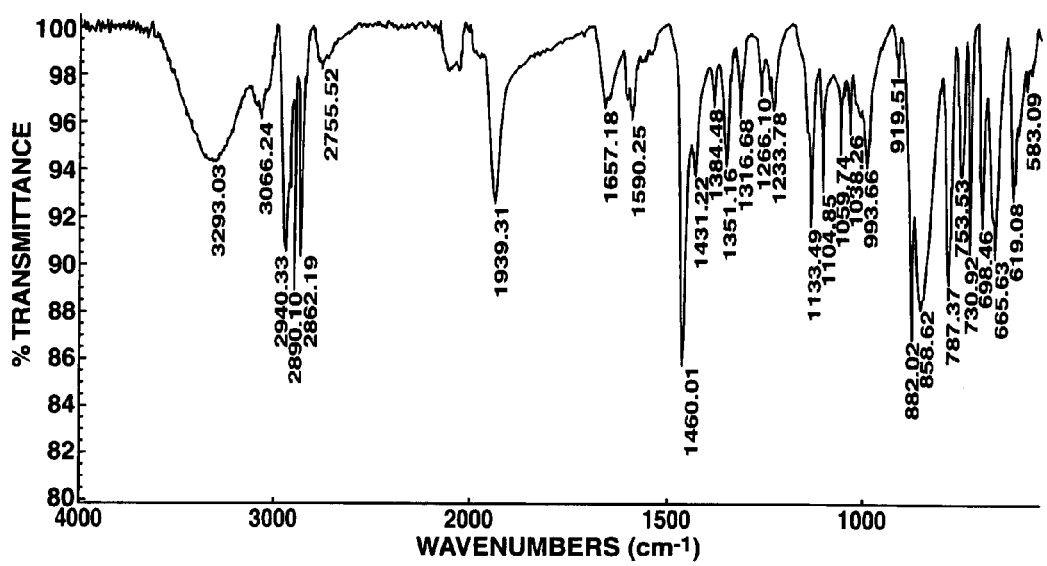
FIG. 1 shows the IR spectrum of the compound produced in Example 5.

The 2,2'-bipyridine derivative having the reactive silyl group of the present invention is represented by the general formula (1):

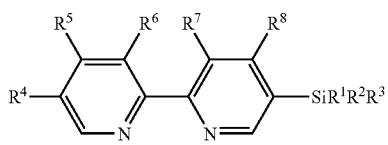
(1)

The $R^1$ and $R^2$ in the general formula (1) independently represents a substituent selected from an unsubstituted or substituted monovalent hydrocarbon group containing 1 to 10 carbon atoms, an unsubstituted or substituted organoxy group containing 1 to 10 carbon atoms, an unsubstituted or substituted acyloxy group containing 1 to 10 carbon atoms, hydroxy group, a halogen atom, hydrogen atom, mercapto group, an unsubstituted or substituted amino group, cyano group, cyanate group, isocyanate group, thiocyanate group, and isothiocyanate group. $R^3$ represents a substituent selected from an unsubstituted or substituted monovalent aliphatic unsaturated hydrocarbon group containing 2 to 10 carbon atoms, an unsubstituted or substituted organoxy group containing 1 to 10 carbon atoms, an unsubstituted or substituted acyloxy group containing 1 to 10 carbon atoms, hydroxy group, a halogen atom, hydrogen atom, mercapto group, an unsubstituted or substituted amino group, cyano group, cyanate group, isocyanate group, thiocyanate group, and isothiocyanate group.

With regard to $R^1$ and $R^2$, examples of the monovalent hydrocarbon group include straight chain, branched, or cyclic alkyl group, alkenyl group, aryl group, and aralkyl group. With regard to $R^3$, examples of the monovalent aliphatic unsaturated hydrocarbon group include alkenyl group; examples of the organoxy group include alkoxy group, alkenyloxy group, aryloxy group, and aralkyl oxy group. Also exemplified are those groups having at least one of their hydrogen atoms substituted with a halogen atom; examples of the halogen atom include fluorine, chlorine, bromine, and iodine; and examples of the substituted amino group include the amino group having one or more of its hydrogen atoms substituted with the monovalent hydrocarbon group as described above.

Examples of the $R^1$ and $R^2$ include methyl group, ethyl group, propyl group, isopropyl group, butyl group, isobutyl group, tert-butyl group, pentyl group, cyclopentyl group, hexyl group, cyclohexyl group, heptyl group, octyl group, decyl group, vinyl group, allyl group, methallyl group, butenyl group, phenyl group, methoxy group, ethoxy group, n-propoxy group, isopropoxy group, n-butoxy group, isobutoxy group, tert-butoxy group, phenyloxy group, acetoxy group, trifluoroacetoxy group, benzoyloxy group, hydroxy group, chlorine atom, bromine atom, iodine atom, hydrogen atom, mercapto group, dimethylamino group, diethylamino group, cyano group, cyanate group, isocyanate group, thiocyanate group, isothiocyanate group. Examples of the $R^3$ include methoxy group, ethoxy group, propoxy group, isopropoxy group, n-butoxy group, isobutoxy group, tert-butoxy group, acetoxy group, hydroxy group, chlorine atom, bromine atom, iodine atom, hydrogen atom, mercapto group, methylamino group, dimethylamino group, isocyanate group, thiocyanate group, isothiocyanate group, hydroxy group, allyl group, vinyl group, benzyloxy group, 2-phenylethoxy group, phenoxy group, and naphthyloxy group.

The silyl group represented by the $R^1R^2R^3Si$ in the general formula (1) is a reactive silyl group in which at least one of the silicon substituents has reactivity. Examples of the $R^1R^2R^3Si$ group include triethoxysilyl group, trimethoxysilyl group, dimethylsilyl group, diisopropylsilyl group, diethylsilyl group, dimethylsilanol group, diethylsilanol group, diisopropylsilanol group, methyldimethoxysilyl group, dimethylmethoxysilyl group, dimethylchlorosilyl group, diethylchlorosilyl group, dihexylchlorosilyl group, diisopropylchlorosilyl group, methyldichlorosilyl group, cyclohexyldichlorosilyl group, cyclopentyldichlorosilyl group, trivinylsilyl group, and triallylsilyl group.

The $R^4$ in the general formula (1) represents the reactive silyl group represented by the $R^1R^2R^3Si$ as described above, an unsubstituted or substituted monovalent hydrocarbon group containing 1 to 10 carbon atoms, or hydrogen atom; and $R^5$, $R^6$, $R^7$, and $R^8$ independently represent an unsubstituted or substituted monovalent hydrocarbon group containing 1 to 10 carbon atoms or hydrogen atom. As in the case of the $R^1$, examples of the monovalent hydrocarbon group include alkyl group, alkenyl group, aryl group, aralkyl group, as well as those groups having at least one of their hydrogen atoms substituted with a halogen atom. Examples of the $R^4$, $R^5$, $R^6$, $R^7$, and $R^8$ include hydrogen atom, methyl group, ethyl group, propyl group, isopropyl group, butyl group, pentyl group, hexyl group, heptyl group, octyl group, cyclopentyl group, cyclohexyl group, benzyl group, 2-phenylethyl group, 3-phenyl propyl group, phenyl group, tolyl group, vinyl group, allyl group, triethoxysilyl group, trimethoxysilyl group, dimethylsilyl group, diisopropylsilyl group, diethylsilyl group, dimethylsilanol group, diethylsilanol group, diisopropylsilanol group, methyldimethoxysilyl group, dimethylmethoxysilyl group, dimethylchlorosilyl group, diethylchlorosilyl group, dihexylchlorosilyl group, diisopropylchlorosilyl group, methyldichlorosilyl group, cyclohexyldichlorosilyl group, cyclopentyldichlorosilyl group, trivinylsilyl group, and triallylsilyl group.

Examples of the compound represented by the general formula (1) include 5-dimethylsilylbipyridine, 5-dimethylvinylsilyl-2,2'-bipyridine, 5-dimethylethoxysilyl-2,2'-bipyridine, 5-dimethylisopropoxy-2,2'-bipyridine, 5-diisopropylsilyl-2,2'-bipyridine, 5-diphenylsilyl-2,2'-bipyridine, 5-diethylsilyl-2,2'-bipyridine, 5-triethoxysilyl-2,2'-bipyridine, 5-dihexylsilyl-2,2'-bipyridine, 5-bromodibutyl-2,2'-bipyridine, 5-dimethylmercaptosilyl-2,2'-bipyridine, 5-methylethoxyethylsilyl-2,2'-bipyridine, 5-dipropylisobutoxysilyl-2,2'-bipyridine, 5-dimethylpropoxy-2,2'-bipyridine, 5-allyldimethylsilyl-2,2'-bipyridine, 5-hydroxydimethylsilyl-2,2'-bipyridine, 5-(hydroxydiisopropylsilyl)-2,2'-bipyridine, 5-(hydroxydiethylsilyl)-2,2'-bipyridine, 5-(hydroxydihexylsilyl)-2,2'-bipyridine, 5,5'-bis(dimethylsilyl)-2,2'-bipyridine, 5,5'-bis(dimethylvinylsilyl)-2,2'-bipyridine, 5,5'-bis(dimethylethoxysilyl)-2,2'-bipyridine, 5,5'-bis(dimethylisopropoxysilyl)-2,2'-bipyridine, 5,5'-bis(diisopropylsilyl)-2,2'-bipyridine, 5,5'-bis(diphenylsilyl)-2,2'-bipyridine, 5,5'-bis(diethylsilyl)-2,2'-bipyridine, 5,5'-bis(triethoxysilyl)-2,2'-bipyridine, 5,5'-bis(dihexylsilyl)-2,2'-bipyridine, 5,5'-bis(bromodibutylsilyl)-2,2'-bipyridine, 5,5'-bis(dimethylmercaptosilyl)-2,2'-bipyridine, 5,5'-bis(methylethoxyethylsilyl)-2,2'-bipyridine, 5,5'-bis(dipropylisobutoxysilyl)-2,2'-bipyridine, 5,5'-bis(dimethylpropoxy)-2,2'-bipyridine, 5,5'-bis(allyldimethylsilyl)-2,2'-bipyridine, 5,5'-bis-(hydroxydimethylsilyl)-2,2'-bipyridine, 5,5'-bis(hydroxydiisopropylsilyl)-2,2'-bipyridine, 5,5'-bis(hydroxydiethylsilyl)-2,2'-bipyridine, 5,5'-bis(hydroxydihexylsilyl)-2,2'-bipyridine, 5-hydroxydiisopropylsilyl-5'-dimethylvinylsilyl-2,2'-bipyridine, and 5-hydroxyisopropylsilyl-5'-dimethylallylsilyl-2,2'-bipyridine.

The method used for producing the compound represented by the general formula (1) of the present invention is not particularly limited. For example, the compound represented by the general formula (1) wherein $R^4$ is a monovalent hydrocarbon group of hydrogen atom may be produced by reacting a 5-halo-2,2'-bipyridine derivative represented by the following general formula (2):

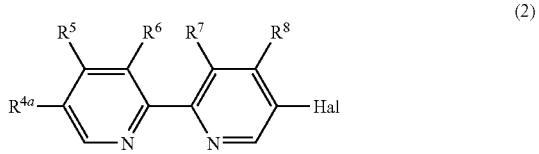

with a metal or a metallo-organic to produce a 5-metallo-2, 2'-bipyridine, and reacting the 5-metallo-2,2'-bipyridine with a silicon compound represented by the general formula (3):

$$XSiR^1R^2R^3 \qquad (3).$$

The Hal in the general formula (2) represents chlorine atom, bromine atom, or iodine atom, $R^{4a}$ represents an unsubstituted or substituted monovalent hydrocarbon group containing 1 to 10 carbon atoms or hydrogen atom, and $R^5$, $R^6$, $R^7$, and $R^8$ are an unsubstituted or substituted monovalent hydrocarbon group containing 1 to 10 carbon atoms or hydrogen atom as defined above. Examples of the $R^{4a}$, $R^5$, $R^6$, $R^7$, and $R^8$ include hydrogen atom, methyl group, ethyl group, propyl group, isopropyl group, butyl group, pentyl group, hexyl group, heptyl group, octyl group, cyclopentyl group, cyclohexyl group, 2-phenylethyl group 3-phenyl propyl group, phenyl group, tolyl group, vinyl group, and allyl group. Examples of the compound represented by the general formula (2) include 5-chlorobipyridine, 5-bromo-2,2'-bipyridine, 5-iodo-2,2'-bipyridine, 3-methyl-5-bromo-2,2'-bipyridine, 4-methyl-5-bromo-2,2'-bipyridine, 3-ethyl-5-bromo-2, 2'-bipyridine, 4-ethyl-5-bromo-2,2'-bipyridine, 3-methyl-5-chloro-2,2'-bipyridine, 3-methyl-5-iodo-2,2'-bipyridine, 3-allyl-5-bromo-2,2'-bipyridine, 3-vinyl-5-bromo-2,2'-bipyridine, and 3-phenyl-5-bromo-2,2'-bipyridine.

The X in the general formula (3) represents a halogen atom or an organoxy group containing 1 to 10 carbon atoms, and $R^1$, $R^2$, and $R^3$ are as defined above for the formula (1). Examples of the X include chlorine atom, bromine atom, iodine atom, methoxy group, ethoxy group, isopropoxy group, and phenoxy group.

Examples of the compound represented by the general formula (3) include chlorotrimethoxysilane, chlorotriethoxysilane, chlorodimethylsilane, chlorodiethylsilane, chlorodimethylphenylsilane, methylethylchlorosilane, chlorodiisopropylsilane, dimethoxychlorosilane, methylphenylchlorosilane, dimethylvinylchlorosilane, benzylmethylchlorosilane, diphenylvinylchlorosilane, diethoxychlorosilane, diphenylchlorosilane, tert-butylmethylchlorosilane, allyldimethylchlorosilane, dimethyldichlorosilane, diisopropyldichlorosilane, tert-butyldichlorosilane, diisopropyldimethoxysilane, diethyldiethoxysilane, dimethyldimethoxysilane, and diisobutyldimethoxysilane.

In a method for producing the 5-metallo-2,2'-bipyridine derivative, this 5-metallo-2,2'-bipyridine derivative is obtained by reacting the 5-halo-2,2'-bipyridine derivative represented by the general formula (2) with a metal or a metallo-organic. Examples of the metal or the metallo-organic include n-butyl lithium, sec-butyl lithium, t-butyl lithium, methyl lithium, phenyl lithium, metal lithium, metal magnesium, methyl magnesium chloride, and methyl magnesium bromide. The metal or the metallo-organic is preferably used at an amount of 1 to 10 moles, and in particular, at 1 to 1.5 moles in relation to 1 mole of the compound represented by the general formula (2). This reaction is preferably conducted at a temperature of 100 to −100° C., and in particular, at −30 to −80° C. preferably for a reaction time of 30 minutes to 10 hours, and in particular, for 30 minutes to 1 hour preferably in a solvent such as an ether-based solvent or a hydrocarbon-based solvent, for example, diethylether, tetrahydrofuran, hexane, pentane, or a mixture thereof.

Next, the resulting 5-metallo-2,2'-bipyridine derivative is reacted with the compound represented by the general formula (3) to produce the compound represented by the general formula (1) wherein $R^4$ is a monovalent hydrocarbon group. In this case, the compound represented by the general formula (3) is preferably used at 1 to 10 moles, and in particular, at 1.5 to 3 moles in relation to 1 mole of the compound represented by the general formula (2), and the reaction is preferably conducted at a temperature of −100 to 100° C., and in particular, at 0 to 20° C. preferably for a reaction time of 1 to 20 hours, and in particular, for 1 to 3 hours preferably in a solvent of an ether-based solvent or a hydrocarbon-based solvent such as diethylether, tetrahydrofuran, hexane, pentane, or a mixture thereof.

When $R^4$ is a substituent represented by $R^1R^2R^3Si$, the compound represented by the general formula (1) of the present invention may also be produced reacting the 5,5'-dihalo-2,2'-bipyridine derivative represented by the following general formula (4) with a metal or a metallo-organic to produce a 5,5'-dimetallo-2,2'-bipyridine, and then reacting the resulting 5,5'-dimetallo-2,2'-bipyridine with the silicon compound represented by the general formula (3).

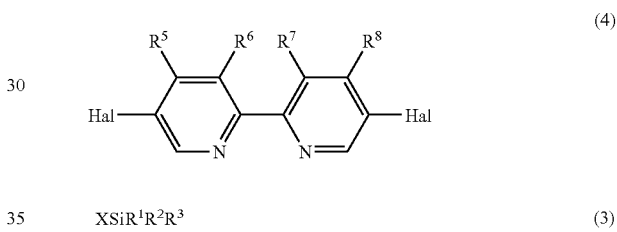

$$XSiR^1R^2R^3 \qquad (3)$$

In the general formula (4), Hal represents chlorine atom, bromine atom, or iodine atom, and $R^5$, $R^6$, $R^7$, and $R^8$ independently represent an unsubstituted or substituted monovalent hydrocarbon group containing 1 to 10 carbon atoms or hydrogen atom as defined above. Examples of the $R^5$, $R^6$, $R^7$, and $R^8$ include hydrogen atom, methyl group, ethyl group, propyl group, isopropyl group, butyl group, pentyl group, hexyl group, heptyl group, octyl group, cyclopentyl group, cyclohexyl group, 2-phenylethyl group 3-phenylpropyl group, phenyl group, tolyl group, vinyl group, and allyl group. Examples of the compound represented by the general formula (4) include 5,5'-dichloro-2,2'-bipyridine, 5,5'-dibromo-2,2'-bipyridine, 5,5'-diiodo-2,2'-bipyridine, 3-methyl-5,5'-dibromo-2,2'-bipyridine, 4-methyl-5,5'-dibromo-2, 2'-bipyridine, 3-ethyl-5,5'-dibromo-2,2'-bipyridine, 4-ethyl-5,5'-dibromo-2,2'-bipyridine, 3-methyl-5,5'-dichloro-2,2'-bipyridine, 3-methyl-5,5'-diiodo-2,2'-bipyridine, 3-allyl-5, 5'-dibromo-2,2'-bipyridine, 3-vinyl-5,5'-dibromo-2,2'-bipyridine, and 3-phenyl-5,5'-dibromo-2,2'-bipyridine.

In this case, the compound represented by the general formula (4) is first reacted with a metal or a metallo-organic to produce the 5,5'-dimetallo-2,2'-bipyridine derivative. This reaction is conducted by repeating the procedure using the 5-halo-2,2'-bipyridine derivative of the general formula (2) except that the metal or the metallo-organic is preferably used at an amount of 2 to 10 moles, and in particular, at 2 to 3 moles in relation to 1 mole of the compound represented by the formula (4).

The resulting 5,5'-dimetallo-2,2'-bipyridine derivative is reacted with the compound represented by the general formula (3) to produce the compound represented by the general formula (1) wherein the $R^4$ is $SiR^1R^2R^3$. This reaction is conducted by repeating the procedure using the 5-metallo-2, 2'-bipyridine derivative except that the compound represented by the general formula (3) is preferably used at an amount of 1.5 to 10 moles, and in particular, at 2 to 3 moles in relation to 1 mole of the compound represented by the general formula (2).

The 2,2'-bipyridine derivative having a reactive silyl group represented by the general formula (1) is also useful as a ligand of a transition metal complex having at least one such ligand, and the transition metal complex is represented by the following general formula (5):

In the general formula (5), M represents a transition metal such as manganese, iron, ruthenium, osmium, cobalt, rhodium, iridium, nickel, palladium, platinum, or copper, and most preferably ruthenium. X is selected from a halogen atom, thiocyanate group, thioisocyanate group, hydroxy group, cyano group, cyanate group, isocyanate group, and carbonyl group. n is an integer of 1 to 3. $L^1$ is a 2,2'-bipyridine derivative having a reactive silyl group represented by represented by the general formula (1). $L^2$ is a 2,2'-bipyridine derivative represented by the general formula (6) wherein $R^9$, $R^{10}$, $R^{11}$, $R^{12}$, $R^{13}$, $R^{14}$, $R^{15}$, and $R^{16}$ are independently an unsubstituted or substituted monovalent hydrocarbon group containing 1 to 20 carbon atoms or hydrogen atom). m is an integer of 0 to 3, p is an integer of 0 to 2, n+p is an integer of 1 to 3.

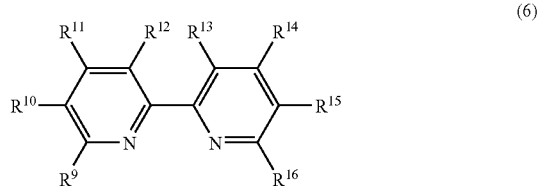

Examples of the compound represented by the general formula (6) include 2,2'-bipyridine, 4,4'-dicarboxy-2,2'-bipyridine, 4,4'-dimethyl-2,2'-bipyridine, 4,4'-diethyl-2,2'-bipyridine, 4,4'-dibromo-2,2'-bipyridine, 4-bromo-2,2'-bipyridine, 4-methyl-2,2'-bipyridine, 5,5'-dicarboxy-2,2'-bipyridine, 5,5'-dimethyl-2,2'-bipyridine, 5,5'-dibromo-2,2'-bipyridine, 5-carboxy-2,2'-bipyridine, 5-methyl-2,2'-bipyridine, 4,4'-dinonanyl-2,2'-bipyridine, 4,4'-bis(2-(4-hexyloxy)-styryl)-2,2'-bipyridine, 4,4'-bis(2-(4-methoxy)-styryl)-2,2'-bipyridine, 4,4'-bis(2-(4-tert-butoxy)-styryl)-2,2'-bipyridine, and 4,4'-bis(5-hexyl thiophene-2-yl-styryl)-2,2'-bipyridine.

Examples of the compound represented by the general formula (5) include chlorobis(5-triethoxysilyl-2,2'-bipyridine) manganese, chlorobis(5-chlorodiisopropylsilyl-2,2'-bipyridine) manganese, chlorobis(5-hydroxydiisopropylsilyl-2,2'-bipyridine) manganese, dichlorobis(5-triethoxysilyl-2,2'-bipyridine) ruthenium, dichlorobis(5-dimethylsilyl-2,2'-bipyridine) ruthenium, dichlorobis(5-diisopropylsilyl-2,2'-bipyridine) ruthenium, dichlorobis(5-diisobutylsilyl-2,2'-bipyridine) ruthenium, dichlorobis(5-chlorodiisopropylsilyl-2,2'-bipyridine) ruthenium, dichlorobis(5-hydroxydiisopropylsilyl-2,2'-bipyridine) ruthenium, dichlorobis(5-hydroxydiethylsilyl-2,2'-bipyridine) ruthenium, dibromobis(5-triethoxysilyl-2,2'-bipyridine) ruthenium, dibromobis(5-dimethylsilyl-2,2'-bipyridine) ruthenium, dibromobis(5-diisopropylsilyl-2,2'-bipyridine) ruthenium, dibromobis(5-diisobutylsilyl-2,2'-bipyridine) ruthenium, dibromobis(5-chlorodiisopropylsilyl-2,2'-bipyridine) ruthenium, dibromobis(5-hydroxydiisopropylsilyl-2,2'-bipyridine) ruthenium, dibromobis(5-hydroxydiethylsilyl-2,2'-bipyridine) ruthenium, dicyanobis(5-triethoxysilyl-2,2'-bipyridine) ruthenium, dicyanobis(5-dimethylsilyl-2,2'-bipyridine) ruthenium, dicyanobis(5-diisopropylsilyl-2,2'-bipyridine) ruthenium, dicyanobis(5-diisobutylsilyl-2,2'-bipyridine) ruthenium, dicyanobis(5-chlorodiisopropylsilyl-2,2'-bipyridine) ruthenium, dicyanobis(5-hydroxydiisopropylsilyl-2,2'-bipyridine) ruthenium, dicyanobis(5-hydroxydiethylsilyl-2,2'-bipyridine) ruthenium, dicyanatobis(5-triethoxysilyl-2,2'-bipyridine) ruthenium, dicyanatobis(5-dimethylsilyl-2,2'-bipyridine) ruthenium, dicyanatobis(5-diisopropylsilyl-2,2'-bipyridine) ruthenium, dicyanatobis(5-diisobutylsilyl-2,2'-bipyridine) ruthenium, dicyanatobis(5-chlorodiisopropylsilyl-2,2'-bipyridine) ruthenium, dicyanatobis(5-hydroxydiisopropylsilyl-2,2'-bipyridine) ruthenium, dicyanatobis(5-hydroxydiethylsilyl-2,2'-bipyridine) ruthenium, dithiocyanatobis(5-triethoxysilyl-2,2'-bipyridine) ruthenium, dithiocyanatobis(5-dimethylsilyl-2,2'-bipyridine) ruthenium, dithiocyanatobis(5-diisopropylsilyl-2,2'-bipyridine) ruthenium, dithiocyanatobis(5-diisobutylsilyl-2,2'-bipyridine) ruthenium, dithiocyanatobis(5-chlorodiisopropylsilyl-2,2'-bipyridine) ruthenium, dithiocyanatobis(5-hydroxydiisopropylsilyl-2,2'-bipyridine) ruthenium, dithiocyanatobis(5-hydroxydiethylsilyl-2,2'-bipyridine) ruthenium, dithioisocyanatobis(5-triethoxysilyl-2,2'-bipyridine) ruthenium, dithioisocyanatobis(5-dimethylsilyl-2,2'-bipyridine) ruthenium, dithioisocyanatobis(5-diisopropylsilyl-2,2'-bipyridine) ruthenium, dithioisocyanatobis(5-diisobutylsilyl-2,2'-bipyridine) ruthenium, dithioisocyanatobis(5-chlorodiisopropylsilyl-2,2'-bipyridine) ruthenium, dithioisocyanatobis(5-hydroxydiisopropylsilyl-2,2'-bipyridine) ruthenium, dithioisocyanatobis(5-hydroxydiethylsilyl-2,2'-bipyridine) ruthenium, dihydroxy bis(5-triethoxysilyl-2,2'-bipyridine) ruthenium, dihydroxy bis(5-dimethylsilyl-2,2'-bipyridine) ruthenium, dihydroxy bis(5-diisopropylsilyl-2,2'-bipyridine) ruthenium, dihydroxy bis(5-diisobutylsilyl-2,2'-bipyridine) ruthenium, dihydroxy bis(5-chlorodiisopropylsilyl-2,2'-bipyridine) ruthenium, dihydroxy bis(5-hydroxydiisopropylsilyl-2,2'-bipyridine) ruthenium, dihydroxy bis(5-hydroxydiethylsilyl-2,2'-bipyridine) ruthenium, dichlorobis(5,5'-bis(triethoxysilyl)-2,2'-bipyridine) ruthenium, dichlorobis(5,5'-bis(chlorodiisopropylsilyl)-2,2'-bipyridine) ruthenium, dichlorobis(5,5'-bis(hydroxydiisopropylsilyl)-2,2'-bipyridine) ruthenium, dichlorobis(5,5'-bis(hydroxydiethylsilyl)-2,2'-bipyridine) ruthenium, dichlorobis(5-hydroxydiisopropylsilyl-5'-dimethylvinylsilyl-2,2'-bipyridine) ruthenium, dichlorobis(5-hydroxydiisopropylsilyl-5'-allyl dimethylsilyl-2,2'-bipyridine) ruthenium, dichlorotris(5-triethoxysilyl-2,2'-bipyridine) ruthenium, dichlorotris(5-hydroxydiisopropylsilyl-2,2'-bipyridine) ruthenium, dichlorobis(5-triethoxysilyl-2,2'-bipyridine) iron, dichlorobis(5-chlorodiisopropylsilyl-2,2'-bipyridine) iron, dichlorobis(5-hydroxydiisopropylsilyl-2,2'-bipyridine) iron, dichlorobis(5-hydroxydiethylsilyl-2,2'-bipyridine) iron, dichlorobis(5,5'-triethoxysilyl-2,2'-bipyridine) iron, dichlorobis(5,5'-chlorodiisopropylsilyl-2,2'-bipyridine) iron, dichlorobis(5,5'-hydrbxydiisopropylsilyl-2,2'-bipyridine) iron, dichlorobis(5,5'-hydroxydiethylsilyl-2,2'-bipyridine) iron, dibromobis(5-triethoxysilyl-2,2'-bipyridine) iron, dibromobis(5-dimethylsilyl-2,2'-bipyridine) iron, dibromobis(5-diisopropylsilyl-2,2'-bipyridine) iron, dibromobis(5-diisobutylsilyl-2,2'-bipyridine) iron, dibromobis(5-chlorodiisopropylsilyl-2,2'-bipyridine) iron, dibromobis(5-hydroxydiisopropylsilyl-2,2'-bipyridine) iron, dibromobis(5-hydroxydiethylsilyl-2,2'-bipyridine) iron, dicyanobis(5-triethoxysilyl-2,2'-bipyridine) iron, dicyanobis(5- dimethylsilyl-2,2'-bipyridine) iron, dicyanobis(5-diisopropylsilyl-2,2'-bipyridine) iron, dicyanobis(5-diisobutylsilyl-2,2'-bipyridine) iron, dicyanobis(5-chlorodiisopropylsilyl-2,2'-bipyridine) iron, dicyanobis(5-hydroxydiisopropylsilyl-2,2'-bipyridine) iron, dicyanobis(5-hydroxydiethylsilyl-2,2'-bipyridine) iron, dicyanatobis(5-triethoxysilyl-2,2'-bipyridine) iron, dicyanatobis(5-dimethylsilyl-2,2'-bipyridine) iron, dicyanatobis(5-diisopropylsilyl-2,2'-bipyridine) iron, dicyanatobis(5-diisobutylsilyl-2,2'-bipyridine) iron, dicyanatobis(5-chlorodiisopropylsilyl-2,2'-bipyridine) iron, dicyanatobis(5-hydroxydiisopropylsilyl-2,2'-bipyridine) iron, dicyanatobis(5-hydroxydiethylsilyl-2,2'-bipyridine) iron, dithiocyanatobis(5-triethoxysilyl-2,2'-bipyridine) iron, dithiocyanatobis(5-dimethylsilyl-2,2'-bipyridine) iron, dithiocyanatobis(5-diisopropylsilyl-2,2'-bipyridine) iron, dithiocyanatobis(5-diisobutylsilyl-2,2'-bipyridine) iron, dithiocyanatobis(5-chlorodiisopropylsilyl-2,2'-bipyridine) iron, dithiocyanatobis(5-hydroxydiisopropylsilyl-2,2'-bipyridine) iron, dithiocyanatobis(5-hydroxydiethylsilyl-2,2'-bipyridine) iron, dithioisocyanatobis(5-triethoxysilyl-2,2'-bipyridine) iron, dithioisocyanatobis(5-dimethylsilyl-2,2'-bipyridine) iron, dithioisocyanatobis(5-diisopropylsilyl-2,2'-bipyridine) iron, dithioisocyanatobis(5-diisobutylsilyl-2,2'-bipyridine) iron, dithioisocyanatobis(5-chlorodiisopropylsilyl-2,2'-bipyridine) iron, dithioisocyanatobis(5-hydroxydiisopropylsilyl-2,2'-bipyridine) iron, dithioisocyanatobis(5-hydroxydiethylsilyl-2,2'-bipyridine) iron, dihydroxy bis(5-triethoxysilyl-2,2'-bipyridine) iron, dihydroxy bis(5-dimethylsilyl-2,2'-bipyridine) iron, dihydroxy bis(5-diisopropylsilyl-2,2'-bipyridine) iron, dihydroxy bis(5-diisobutylsilyl-2,2'-bipyridine) iron, dihydroxy bis(5-chlorodiisopropylsilyl-2,2'-bipyridine) iron, dihydroxy bis(5-hydroxydiisopropylsilyl-2,2'-bipyridine) iron, dihydroxy bis(5-hydroxydiethylsilyl-2,2'-bipyridine) iron, dichlorobis(5,5'-bis(triethoxysilyl)-2,2'-bipyridine) iron, dichlorobis(5,5'-bis(chlorodiisopropylsilyl)-2,2'-bipyridine) iron, dichlorobis(5,5'-bis(hydroxydiisopropylsilyl)-2,2'-bipyridine) iron, dichlorobis(5,5'-bis(hydroxydiethylsilyl)-2,2'-bipyridine) iron, dichlorobis(5-hydroxydiisopropylsilyl-5'-dimethylvinylsilyl-2,2'-bipyridine) iron, dichlorobis(5-triethoxysilyl-2,2'-bipyridine) osmium, dichlorobis(5-chlorodiisopropylsilyl-2,2'-bipyridine) osmium, dichlorobis(5-hydroxydiisopropylsilyl-2,2'-bipyridine) osmium, dichlorobis(5-hydroxydiethylsilyl-2,2'-bipyridine) osmium, dichlorobis(5,5'-triethoxysilyl-2,2'-bipyridine) osmium, dichlorobis(5,5'-chlorodiisopropylsilyl-2,2'-bipyridine) osmium, dichlorobis(5,5'-hydroxydiisopropylsilyl-2,2'-bipyridine) osmium, dichlorobis(5,5'-hydroxydiethylsilyl-2,2'-bipyridine) osmium, dichlorobis(5-triethoxysilyl-2,2'-bipyridine) cobalt, dichlorobis(5-chlorodiisopropylsilyl-2,2'-bipyridine) cobalt, dichlorobis(5-hydroxydiisopropylsilyl-2,2'-bipyridine) cobalt, dichlorobis(5-hydroxydiethylsilyl-2,2'-bipyridine) cobalt, dichlorobis(5,5'-bis(triethoxysilyl)-2,2'-bipyridine) cobalt, (5,5'-bis(chlorodiisopropylsilyl)-2,2'-bipyridine) cobalt, dichlorobis(5,5'-bis(hydroxydiisopropylsilyl)-2,2'-bipyridine) cobalt, dichlorobis(5,5'-bis(hydroxydiethylsilyl)-2,2'-bipyridine) cobalt, chlorobis(5-triethoxysilyl-2,2'-bipyridine) iridium, chlorobis(5-chlorodiisopropylsilyl-2,2'-bipyridine) iridium, chlorobis(5-hydroxydiisopropylsilyl-2,2'-bipyridine) iridium, dichloro(5-triethoxysilyl-2,2'-bipyridine) palladium, dichloro(5-chlorodiisopropylsilyl-2,2'-bipyridine) palladium, dichloro(5-hydroxydiisopropylsilyl-2,2'-bipyridine) palladium, chlorobis(5-triethoxysilyl-2,2'-bipyridine) rhodium, chlorobis(5-chlorodiisopropylsilyl-2,2'-bipyridine) rhodium, chlorobis(5-hydroxydiisopropylsilyl-2,2'-bipyridine) rhodium, dichloro(5-triethoxysilyl-2,2'-bipyridine) nickel, dichloro(5-chlorodiisopropylsilyl-2,2'-bipyridine) nickel, dichloro(5-hydroxydiisopropylsilyl-2,2'-bipyridine) nickel, dichloro(5-triethoxysilyl-2,2'-bipyridine) copper, dichloro(5-chlorodiisopropylsilyl-2,2'-bipyridine) copper, dichloro(5-hydroxydiisopropylsilyl-2,2'-bipyridine) copper, dichloro(5-triethoxysilyl-2,2'-bipyridine) platinum, dichloro(5-chlorodiisopropylsilyl-2,2'-bipyridine) platinum, dichloro(5-hydroxydiisopropylsilyl-2,2'-bipyridine) platinum, dichlorobis(5-hydroxydiisopropylsilyl-2,2'-bipyridine)(4,4'-dinonanyl-2,2'-bipyridine) ruthenium, dichlorobis(5-hydroxydiisopropylsilyl-2,2'-bipyridine)(2-(4-hexyloxy)-styryl-2,2'-bipyridine) ruthenium, dichlorobis(5-hydroxydiisopropylsilyl-2,2'-bipyridine)((4-methoxy)-styryl-2,2'-bipyridine) ruthenium, dichlorobis(5-hydroxydiisopropylsilyl-2,2'-bipyridine)(2-(4-tert-butoxy)-styryl-2,2'-bipyridine) ruthenium, dichlorobis(5-hydroxydiisopropylsilyl-2,2'-bipyridine)(5-hexyl thiophene-2-yl-styryl-2,2'-bipyridine) ruthenium, dithiocyanatobis(5-hydroxydiisopropylsilyl-2,21-bipyridine)-(4,4'-dinonanyl-2, 2'-bipyridine) ruthenium, dithiocyanatobis(5-hydroxydiisopropylsilyl-2,2'-bipyridine)-(2-(4-hexyloxy)-styryl-2,2'-bipyridine) ruthenium, dithiocyanatobis(5-hydroxydiisopropylsilyl-2,2'-bipyridine)-((4-methoxy)-styryl-2,2'-bipyridine) ruthenium, dithiocyanatobis(5-hydroxydiisopropylsilyl-2,2'-bipyridine)-(2-(4-tert-butoxy)-styryl-2,2'-bipyridine) ruthenium, and dithiocyanatobis(5-hydroxydiisopropylsilyl-2,2'-bipyridine)-(5-hexyl thiophene-2-yl-styryl-2,2'-bipyridine) ruthenium.

The transition metal complex represented by the general formula (5) of the present invention can be produced by various methods. Exemplary methods include those as described below.

The transition metal complex represented by the general formula (5) wherein p is 0 can be produced as shown by the following reaction scheme by reacting the 2,2'-bipyridine derivative represented by the general formula (1) with the metal salt represented by the $(X)_mM$. Examples of the metal salt represented by the $(X)_mM$ include manganese chloride tetrahydrate, iron(III) chloride, ruthenium chloride trihydrate, osmium chloride trihydrate, cobalt chloride(III), rhodium chloride trihydrate, iridium trichloride, palladium (II) chloride, nickel chloride hexahydrate, platinum(IV) chloride, and copper(II) chloride.

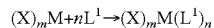

$$(X)_mM + nL^1 \rightarrow (X)_mM(L^1)_n$$

In this reaction scheme, M, X, $L^1$, m, and n are as defined above for the general formula (5).

The transition metal complex represented by the general formula (5) wherein p is 1 or 2 can be produced as shown by the following reaction scheme by reacting the 2,2'-bipyridine derivative represented by the general formula (1) with the metal salt represented by the $(X)_mM$. Examples of the metal salt represented by the $(X)_mM$ is the same as those as described above.

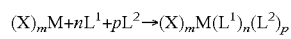

$$(X)_mM + nL^1 + pL^2 \rightarrow (X)_mM(L^1)_n(L^2)_p$$

In this reaction scheme, M, X, $L^1$, $L^2$, m, n, and p are as defined above for the general formula (5). In this reaction, $L^1$ and $L^2$ may be sequentially added to the metal salt represented by the $(X)_mM$ in any order, or all of $(X)_mM$, $L^1$, and $L^2$ may be reacted at once.

The compound represented by the general formula (5) may also be synthesized by ligand exchange using a transition metal complex. More specifically, the compound represented by the general formula (5) may be synthesized as shown by the following reaction scheme by reacting the 2,2'-bipyridine derivative represented by the general formula (1) and the transition metal complex represented by the $(X)_mM(L)_q$.

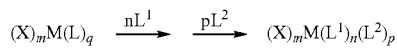

Examples of the transition metal complex represented by the $(X)_mM(L)_q$ include dichlorotetrakis(dimethyl sulfoxide) ruthenium(II), dichloro(p-cymene) ruthenium(II) dimer, dichlorobis(triphenylphosphine) palladium(II), chlorocyclooctadienerhodium(I) dimer, dibromotetrakis(dimethyl sulfoxide)osmium(II), and dichlorobis(ethylenediamine) nickel(II).

In the reaction schemes as described above, M, X, $L^1$, $L^2$, m, n, and q are as defined above for the general formula (5). q is an integer of 1 to 6, and L represents a neutral ligand such as dimethyl sulfoxide, p-cymene, triphenylphosphine, cyclooctadiene, and ethylenediamine. In this reaction, $L^1$ and $L^2$ may be sequentially added to the transition metal complex represented by the $(X)_mM(L)_q$ in any order, or all of $(X)_mM(L)_q$, $L^1$, and $L^2$ may be reacted at once.

With regard to the metal complex represented by the general formula (5) produced by the methods as described above, a part or all of X can be converted to a different substituent, for example, by adding a metal salt or ammonium salt to the compound represented by the $(X)_mM(L^1)_n(L^2)_p$ synthesized by the reaction with a metal halide salt. Examples of such metal salt or ammonium salt include ammonium thiocyanate, potassium thiocyanide, sodium thiocyanide, sodium cyanate, ammonium cyanate, potassium cyanate, sodium cyanide, ammonium cyanide, potassium cyanide, ammonium hydroxide, sodium hydroxide, and potassium hydroxide.

The transition metal complex of the present invention has a reactive silyl group which can be covalently bonded to the support (carrier), and the transition metal complex can be immobilized for use as a supported-type transition metal catalyst. The support as used herein means a solid support to which the transition metal complex of the present invention can be covalently bonded by the silyl group. The solid support may comprise, for example, an inorganic material such as silica, alumina, titania, zirconia, montmorillonite, clay, or zeolite; an organic-inorganic hybrid material such as silica or polysiloxane having an organofunctional group; or an organic polymer such as a modified polystyrene, a modified rubber or a dendrimer having hydroxy group or carboxyl group.

The immobilization of the transition metal complex of the present invention to the support may be accomplished by bringing the transition metal complex of the present invention in contact with the support material as described above for chemical reaction between the transition metal complex and the support material. The support may be preliminarily treated for hydrophilization by UV ozone treatment, plasma treatment, or corona discharge treatment to thereby increase amount of the transition metal complex immobilized on the support. This pretreatment also imparts reactivity with the support material having no hydroxy group or carboxyl group.

In another method of immobilization, the 2,2'-bipyridine derivative having a reactive silyl group of the present invention is first bonded to the support, and the transition metal salt or the transition metal complex is then reacted with the 2,2'-bipyridine derivative on the support. This method is capable of producing a transition metal catalyst supported on the support without isolating the transition metal complex.

The resulting supported-type transition metal catalyst can be used in various chemical reactions such as oxidation, reduction, coupling, and polymerization. Since the transition metal catalyst is immobilized on the support, isolation of the product is facilitated, and the catalyst can be readily collected and recycled.

The transition metal complex of the present invention is capable of binding to a wide-gap oxide semiconductor such as titanium oxide, tin oxide, or zinc oxide. The transition metal complex is also capable of absorbing visible light. Therefore, the transition metal complex can be used as a dye in a dye-sensitized photoelectric conversion device.

The dye-sensitized photoelectric conversion device is described, for example, in the Japanese Patent No. 3731752. More specifically, fine particles of a wide gap oxide semiconductor which is typically indium tin oxide or fluorine-doped tin oxide are coated on a glass or plastic substrate having a transparent conducting thin film formed on its surface to a thickness of 1 to 50 μm, and the transition metal complex of the present invention is contacted with the fine particles of the wide gap oxide semiconductor to thereby bind the transition metal complex to the fine particles and prepare the working electrode. This working electrode and the counter electrode are bonded by using an encapsulating material, and after introducing an electrolyte, the inlet used for this introduction is encapsulated to complete the assembly of the dye-sensitized photoelectric conversion device.

The counter electrode preferably comprises a substrate having an electrochemically catalytic platinum or carbon on its surface. More specifically, the counter electrode may comprise a platinum plate, a titanium plate having a platinum thin film formed thereon, a glass or plastic substrate having a transparent electroconductive thin film having a platinum thin film formed thereon, or graphite.

Examples of the encapsulating material include a thermosetting resin such as epoxy resin, and a thermofusible resin such as ionomer resin. The thickness of the encapsulating material between the working electrode and the counter electrode is not particularly limited as long as it is more than the thickness of the wide gap semiconductor thin film. The thickness, however, is typically in the range of 1 to 100 μM.

Typical electrolytes used include an organic solution having iodine dissolved therein and an ionic liquid. However, iodine may be replaced with bromine or other redox system depending on the type of the transition metal complex or the wide gap semiconductor. Examples of the organic solution include acetonitrile, propionitrile, valeronitrile, methoxy propionitrile, butyrolactone, ethylene carbonate, and propylene carbonate, and examples of the ionic liquid include 1,3-dimethylimidazolium iodide, 1-ethyl-3-methylimidazolium iodide, 1-propyl-3-methylimidazolium iodide, 1-butyl-3-methylimidazolium iodide, 1-hexyl-3-methylimidazolium iodide, 1-butyl-3-methylimidazolium tetrafluoroborate, 1-butyl-3-methylimidazolium hexafluorophosphate, 1-butyl-3-methylimidazolium trifluoromethanesulfonate, 1-ethyl-3-methylimidazolium thiocyanate, 1-butyl-3-methylimidazolium thiocyanate, 1-ethyl-3-methylimidazolium bis(pentafluoroethyl) sulfonyl) imide, 1-butyl-3-methylimidazolium bis(trifluoromethyl sulfonyl) imide, 1-hexyl-3-methylimidazolium bis(trifluoromethyl sulfonyl) imide, 1-hexyl-3-methylimidazolium tris(pentafluoroethyl) trifluoro-phosphate, 1-butyl-3-methylimidazolium hexafluoroantimonate, 1-propyl-2,3-dimethylimidazolium tris(trifluoromethane-sulfonyl)methide, 1-butyl-3-methylimidazolium dicyanamide, 1-butyl-1-methylpyrrolidinium dicyanamide, and 3-methyl-1-butylpyrrolidinium bis(trifluoromethyl sulfonyl) imide. In addition, an inorganic salt such as lithium iodide, an organic salt such as guanidium thiocyanate or 2,3-dimethyl-1-propylimidazolium iodide, or a basic compound such as 4-tert-butyl pyridine or N-methyl benzimidazole may also be added to the electrolyte for the purpose of improving the performance.

The transition metal complex of the present invention may be used, for example, as an electrochemical device such as an electrochemical sensor for detecting DNA or protein. Exemplary methods used for producing the electrochemical element are as described below.

First, a probe is prepared. This probe comprises an electroconductive substrate having a single strand DNA, a protein, a peptide molecule, an enzyme, or the like bonded to its electroconductive area. The electroconductive substrate may comprise a material such as a metal, for example, gold, silver, copper, aluminum, platinum, or titanium, a semiconductor, for example, silicon or germanium, a transparent electroconductive oxide, for example, indium tin oxide, fluorine-doped tin oxide, aluminum zinc oxide, or indium zinc oxide. Alternatively, the electroconductive substrate may also comprise an insulating material such as glass, quartz, or a ceramic or plastic material having a thin film of such electroconductive material or an organic electroconductive material such as pentacene or poly-2-hexyl thiophene formed thereon.

The probe may be bonded to the electroconductive substrate, for example, by a covalent bond such as ether bond, thioether bond, amide bond, ureido bond, or ester bond optionally with an adequate intervening spacer molecule. This bonding may be accomplished by first bonding the spacer molecule which is capable of reacting with the probe to the electroconductive substrate, and thereafter conducting the reaction between the spacer molecule and the probe. Alternatively, the bond can be established by first bonding the spacer molecule which is capable of reacting with the electroconductive substrate to the probe, and thereafter conducting the reaction between the spacer molecule and the electroconductive substrate.

In the meanwhile, the sample single strand DNA, protein, peptide molecule, or the like is labeled by chemically attaching the transition metal complex of the present invention having a reactive silyl group. This labeling can be accomplished by reacting the sample with the transition metal complex of the present invention either directly or in a way so that an adequate intervening spacer molecule will be present between the sample and the transition metal complex. When the resulting labeled sample molecule is brought in contact with the electroconductive substrate having the probe bonded thereto, the labeled sample molecule is selectively immobilized by hydrogen bond or the like to the area where the probe capable of undergoing a specific interaction such as a single strand DNA having a complimentary sequence or an antibody against the antigen molecule is present.

The thus produced electrochemical sensor functions by the principle as described below. When the sample molecule which is specific for the probe is immobilized in a particular area of the substrate, photoexcitation of the transition metal complex of the present invention bonded to the sample molecule results in the electron transfer from the transition metal complex to the electroconductive substrate, and this electron transfer can be detected as an electric current since electric current is generated in the area where the sample is bonded to the substrate and no electric current is generated in the area where the sample is not bonded to the substrate. As a consequence, the thus produced electrochemical sensor functions as a photoelectrochemical sensor capable of detecting the sample which is specific to the probe that had been bonded to the electroconductive substrate.

The transition metal complex of the present invention is capable of emitting fluorescence or phosphorescence in the excited state, and therefore, this luminescent material can be used, for example, for the light-emission layer of an organic electroluminescent device and the luminescent material of a photochemical sensor. For example, a photochemical sensor can be manufactured by producing an electrochemical device exemplified above using an insulating substrate such as glass, quartz, or a ceramic or plastic material instead of the electroconductive substrate. In this case, the substrate having a probe immobilized thereto that had been produced as in the case of the electrochemical sensor is brought in contact with the sample labeled by the transition metal complex of the present invention except that an insulating substrate is used. Then, the transition metal complex of the present invention bonded to the sample molecule is excited by irradiating with a light beam, and in this instance, luminescence from the transition metal complex can be observed since the substrate comprises an insulating material and electron transfer to the substrate does not take place. Accordingly, amount of the sample molecule that became bonded to the particular area of the substrate can be measured by measuring intensity of the luminescence by a photomultiplier.

EXAMPLES

Next, the present invention is described in further detail by referring to Examples, which by no means limit the scope of the present invention.

Example 1

Preparation of 5-dimethylvinylsilyl-2,2'-bipyridine

Interior of a 100 ml three necked flask equipped with a reflux condenser and a stirrer was purged with nitrogen. To this flask were added 718.8 mg (3.07 mmol) of 5-bromobipyridine and 20 ml of dehydrated diethylether. The reaction mixture was then cooled to −70° C. in a dry ice bath, and 2.0 ml (5.46 mmol) of 2.73M n-butyl lithium was added dropwise in about 10 minutes. After stirring for 30 minutes at the same temperature, 750.0 mg (6.21 mmol) of dimethylvinylchlorosilane was added, and the temperature was gradually elevated to room temperature, and the mixture was stirred for overnight. The reaction was ceased by adding water, and the organic layer was extracted by separation. The resulting solution was dried by magnesium sulfate, concentrated at a reduced pressure by a rotary evaporator, and purified by HPLC to obtain 552.2 mg of yellow solution. After evaluation for NMR spectrum and GC-MS spectrum, the solution was confirmed to be 5-dimethylvinylsilyl-2,2'-bipyridine. The yield was 74.9%. The results are shown below.

$^1$H-NMR (300 MHz, δ in CDCl$_3$): 0.41 (s, 6H), 5.81 (dd, J=20.0 Hz, 3.8 Hz, 1H), 6.12 (dd, J=14.7 Hz, J=3.8 Hz, 1H), 6.30 (dd, J=20.0 Hz, 14.7 Hz, 1H), 7.30 (ddd, J=7.5 Hz, J=4.8 Hz, J=1.2 Hz, 1H), 7.81 (dd, J=7.7 Hz, J=1.9 Hz, 1H), 7.93 (dd, J=7.8 Hz, J=1.8 Hz, 1H), 8.36 (dd, J=7.8 Hz, J=0.9 Hz, 1H), 8.41 (dt, J=7.9 Hz, J=1.0 Hz, 1H), 8.69 (ddd, J=4.8 Hz, J=1.8 Hz, J=0.9 Hz, 1H), 8.76 (dd, J=1.7 Hz, J=1.0 Hz, 1H)

$^{13}$C-NMR (75 MHz, 6 in CDCl$_3$): −3.06, 120.28, 121.11, 123.77, 133.41, 133.81, 136.75, 136.90, 142.62, 149.22, 153.82, 156.25, 156.32

GC-MS (EI) m/z: 240 (M$^+$), 225 (M$^+$-Me), 213, 199

Example 2

Preparation of 5-dimethylsilyl-2,2'-bipyridine

Interior of a 100 ml three necked flask equipped with a reflux condenser and a stirrer was purged with nitrogen. To this flask were added 234.0 mg (1.0 mmol) of 5-bromobipyridine and 7 ml of dehydrated diethylether. The reaction mixture was then cooled to −70° C. in a dry ice bath, and 0.7 ml (1.1 mmol) of 1.58M n-butyl lithium was added dropwise in about 10 minutes. After stirring for 30 minutes at the same temperature, 0.16 ml (1.47 mmol) mg of dimethylvinylchlorosilane (6.21 mmol) was added, and the temperature was gradually elevated to room temperature, and the mixture was stirred for overnight. The reaction was ceased by adding water, and the organic layer was extracted by separation. The resulting solution was dried by magnesium sulfate, concentrated at a reduced pressure by a rotary evaporator, and purified by HPLC to obtain 163.4 mg of colorless solution. After evaluation for NMR spectrum and GC-MS spectrum, the solution was confirmed to be 5-dimethylvinylsilyl-2,2'-bipyridine. The yield was 76.4%. The results are shown below.

$^1$H-NMR (300 MHz, δ in CDCl$_3$): 0.41 (d, J=3.8 Hz, 6H), 4.51 (sept, J=7.6 Hz, J=4.9 Hz, J=1.2 Hz, 1H), 7.31 (ddd, J=7.5 Hz, J=4.8 Hz, J=1.2 Hz, 1H), 7.81 (ddd, J=8.0 Hz, J=7.6 Hz, J=1.7 Hz, 1H), 7.95 (dd, J=7.8 Hz, J=1.8 Hz, 1H), 8.37 (dd, J=7.8 Hz, J=1.0 Hz, 1H), 8.42 (dt, J=7.8 Hz, J=1.2 Hz, 1.0 Hz, 1H), 8.69 (ddd, J=4.8 Hz, J=1.8 Hz, J=0.9 Hz, 1H), 8.76 (dd, J=1.7 Hz, J=1.0 Hz, 1H)

$^{13}$C-NMR (75 MHz, δ in CDCl$_3$): −4.03, 120.34, 121.14, 123.82, 132.46, 136.90, 142.76, 149.22, 153.88, 156.17, 156.54

GC-MS (EI) m/z: 214 (M$^+$), 199 (M$^+$-Me), 184 (M$^+$-Me-Me)

Example 3

Preparation of 5-ethoxydimethylsilyl-2,2'-bipyridine

Interior of a 100 ml three necked flask equipped with a reflux condenser and a stirrer was purged with nitrogen. To this flask were added 711.1 mg (3.04 mmol) of 5-bromobipyridine and 15 ml of dehydrated diethylether, and 5-dimethylsilyl-2,2'-bipyridine was prepared by repeating the procedure of Example 2. To a 100 ml three necked flask equipped with a reflux condenser, thermometer, and a stirrer having its interior replaced with nitrogen was added the thus obtained 5-dimethylsilyl-2,2'-bipyridine, 30 mg of 5% palladium-carbon catalyst, and 15 ml of ethanol. The mixture was stirred at interior temperature of 20 to 30° C. for 20 hours. The catalyst was removed by filtration, and the filtrate was concentrated at a reduced pressure by a rotary evaporator, and purified by HPLC to obtain 560 mg of yellow solution. After evaluation for NMR spectrum and GC-MS spectrum, the solution was confirmed to be 5-dimethylvinylsilyl-2,2'-bipyridine. The yield was 71.4%. The results are shown below.

$^1$H-NMR (300 MHz, δ in CDCl$_3$): 0.45 (s, 6H), 1.21 (t, J=7.0 Hz, 6H), 3.72 (q, J=7.0 Hz, 2H), 7.32 (ddd, J=7.6 Hz, J=4.7 Hz, J=1.1 Hz, 1H), 7.82 (ddd, J=8.0 Hz, J=7.6 Hz, J=1.8 Hz, 1H), 7.99 (dd, J=7.8 Hz, J=1.8 Hz, 1H), 8.39 (dd, 7.84, J=1.8 Hz), 8.42 (dt, J=8.0 Hz, J=1.1 Hz), 8.69 (ddd, J=4.8 Hz, J=1.8 Hz, J=0.8 Hz, 1H), 8.83 (dd, J=1.8 Hz, J=1.0 Hz, 1H)

$^{13}$C-NMR (75 MHz, δ in CDCl$_3$): −1.67, 18.42, 58.88, 120.39, 121.19, 123.86, 132.99, 136.93, 142.31, 149.26, 153.54, 156.18, 156.79

GC-MS (EI) m/z: 258 (M$^+$), 243 (M$^+$-Me), 215, 199, 183

Example 4

Preparation of 5-diisopropylsilyl-2,2'-bipyridine

Interior of a 100 ml three necked flask equipped with a reflux condenser and a stirrer was purged with nitrogen. To this flask were added 702.4 mg (3.0 mmol) of 5-bromobipyridine and 20 ml of dehydrated diethylether. The reaction mixture was then cooled to −70° C. in a dry ice bath, and 1.3 ml (3.2 mmol) of 2.6M n-butyl lithium was added dropwise in about 10 minutes. After stirring for 30 minutes at the same temperature, 1.0 g (6.6 mmol) of diisopropylchlorosilane was added, and the temperature was gradually elevated to room temperature, and the mixture was stirred for overnight. The reaction was ceased by adding water, and the organic layer was extracted by separation. The resulting solution was dried by magnesium sulfate, concentrated at a reduced pressure by a rotary evaporator, and purified by HPLC to obtain 640 mg of colorless solution. After evaluation for NMR spectrum and GC-MS spectrum, the solution was confirmed to be 5-diisopropylsilyl-2,2'-bipyridine. The yield was 79.0%. The results are shown below.

$^1$H-NMR (300 MHz, δ in CDCl$_3$): 1.02 (m, 7H), 1.09 (m, 7H), 4.02 (t, J=3.2 Hz, 1H) 7.31 (ddd, J=7.5 Hz, J=4.7 Hz, J=1.1 Hz, 1H), 7.82 (ddd, J=8.0 Hz, J=7.6 Hz, J=1.7 Hz, 1H), 7.96 (dd, J=7.8 Hz, J=1.8 Hz, 1H), 8.37 (dd, J=7.8 Hz, J=1.0 Hz, 1H), 8.42 (dt, J=7.8 Hz, J=1.2 Hz, 1.0 Hz, 1H), 8.69 (ddd, J=4.8 Hz, J=1.8 Hz, J=0.9 Hz, 1H), 8.77 (dd, J=1.7 Hz, J=1.0 Hz, 1H)

$^{13}$C-NMR (75 MHz, δ in CDCl$_3$): 10.50, 18.36, 18.57, 120.29, 121.11, 123.83, 129.57, 136.93, 144.24, 149.26, 154.91, 156.21, 156.51

GC-MS (EI) m/z: 270 (M$^+$), 227 (M$^+$-CH(CH$_3$)$_2$)

Example 5

Dichlorobis(5-hydroxydiisopropylsilyl-2,2'-bipyridine)-ruthenium (II)

Interior of a 100 ml three necked flask equipped with a reflux condenser and a stirrer was purged with nitrogen. To this flask were added 130.9 mg of 5-diisopropylsilyl-2,2'-bipyridine, 63.3 mg of ruthenium chloride trihydrate, and 8 ml of DMF. After refluxing at 130° C. for 6 hours, the solution was concentrated at a reduced pressure by a rotary evaporator, and the resulting crystals were filtered with diethylether to obtain 151.7 mg of black solid. By evaluation for MALDI-TOFMS, this solid was confirmed to be Ru-bis(5-diisopropyl-2,2'-bipyridine)-dichloride silanol. The yield was 84.3%. In this Example, the ruthenium chloride trihydrate also acted as a catalyst in the course of complex formation, and the diisopropylsilyl group was converted to hydroxydiisopropylsilyl group by dehydrogenation.

MALDI-TOFMS m/z: 744 (M$^+$)

FIG. 1 shows the IR spectrum chart.

Example 6

Dithiocyanatobis(5-hydroxydiisopropylsilyl-2,2'-bipyridine)-ruthenium (II)

Interior of a 100 ml light-shielded three necked flask equipped with a reflux condenser and a stirrer was purged with nitrogen. To this flask were added 117.3 mg of bis(dichlorobis(5-hydroxydiisopropylsilyl-2,2'-bipyridine)-ruthenium (II) and 20 ml of DMF. In the meanwhile, 418.3 mg of sodium thiocyanate was dissolved in 2 ml of distilled water, and this solution was added to the mixture in the flask, and the mixture was refluxed for 6 hours. The reaction mixture was then allowed to cool, and concentrated at a reduced pressure by a rotary evaporator. Water was added, and the solid precipitate was separated by filtration. Purification by silica gel chromatography (CHCl$_3$:MeOH=9:1) was conducted to obtain 50.4 mg of purple solid. By evaluation for MALDI-TOFMS, this solid was confirmed to be dithiocyanato-bis(5-hydroxydiisopropylsilyl-2,2'-bipyridine)-ruthenium (II). The yield was 40.5%.

MALDI-TOFMS m/z: 790 (M$^+$)

Figure 2:
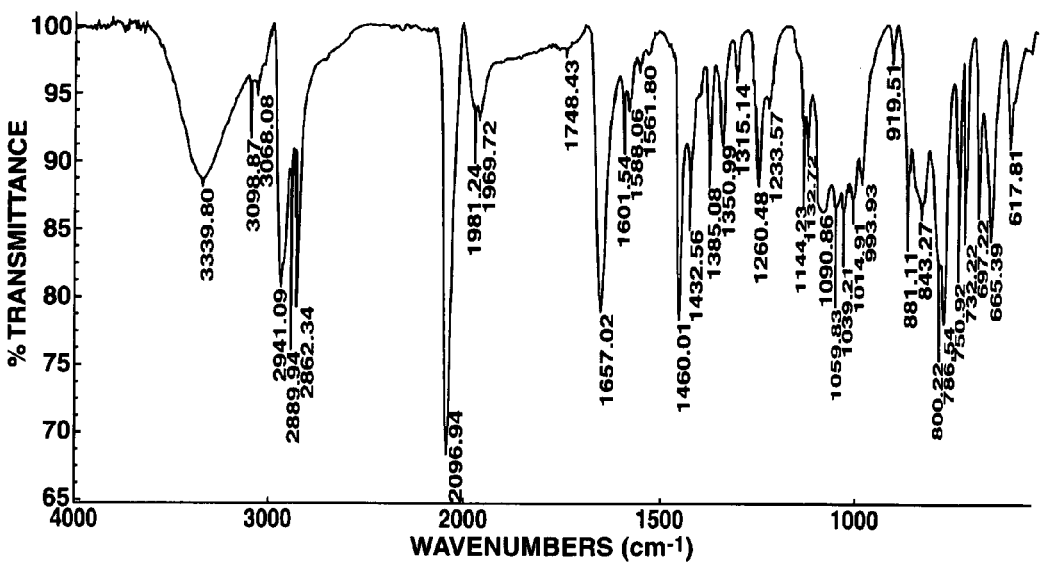
FIG. 2 shows the IR spectrum of the compound produced in Example 6.

FIG. 2 shows the IR spectrum chart.

Japanese Patent Application No. 2008-140803 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A 2,2'-bipyridine derivative having a reactive silyl group represented by the following general formula (1):

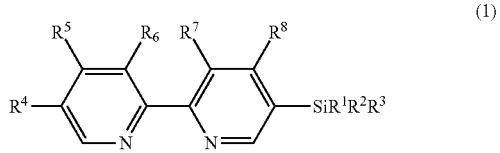
(1)

wherein R$^1$ and R$^2$ independently represent a substituent selected from an unsubstituted or substituted monovalent hydrocarbon group containing 1 to 10 carbon atoms, an unsubstituted or substituted organoxy group containing 1 to 10 carbon atoms, an unsubstituted or substituted acyloxy group containing 1 to 10 carbon atoms, hydroxy group, a halogen atom, hydrogen atom, mercapto group, an unsubstituted or substituted amino group, and isocyanate group; R$^3$ represents a substituent selected from an unsubstituted or substituted monovalent aliphatic unsaturated hydrocarbon group containing 2 to 10 carbon atoms, an unsubstituted or substituted organoxy group containing 1 to 10 carbon atoms, an unsubstituted or substituted acyloxy group containing 1 to 10 carbon atoms, hydroxy group, a halogen atom, hydrogen atom, mercapto group, an unsubstituted or substituted amino group, and isocyanate group R$^4$, R$^5$, R$^6$, R$^7$, and R$^8$ are independently an unsubstituted or substituted monovalent hydrocarbon group containing 1 to 10 carbon atoms or hydrogen atom.

2. The 2,2'-bipyridine derivative having a reactive silyl group according to claim 1 wherein R$^1$ and R$^2$ in the general formula (1) are methyl group.

3. A method of producing a 2,2'-bipyridine derivative having a reactive silyl group represented by the general formula (1) of claim 1 wherein R$^4$ represents an unsubstituted or substituted monovalent hydrocarbon group containing 1 to 10 carbon atoms or hydrogen atom, by reacting a 5-metallo-2,2'-bipyridine derivative produced from a 5-halo-2,2'-bipyridine derivative represented the following general formula (2):

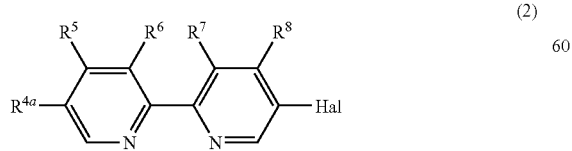
(2)

wherein Hal represents chlorine atom, bromine atom, or iodine atom, R$^{4a}$ represens an unsubstituted or substituted monovalent hydrocarbon group containing 1 to 10 carbon atoms or hydrogen atom, and R$^5$, R$^6$, R$^7$, and R$^8$ are as defined above for the formula (1), with a silicon compound represented by the following general formula (3):

$$XSiR^1R^2R^3 \quad (3)$$

wherein X represents a halogen atom or an organoxy group containing 1 to 10 carbon atoms, and R$^1$, R$^2$, and R$^3$ independently represent the same substituent as the one defined for formula (1).

4. A method of producing a 2,2'-bipyridine derivative having a reactive silyl group represented by the general formula (1) of claim 1 wherein R$^4$ represents a reactive silyl group represented by the formula: R$^1$R$^2$R$^3$Si, by reacting a 5,5'-dimetallo-2,2'-bipyridine derivative produced from a 5,5'-dihalo-2,2'-bipyridine derivative represented the following general formula (4):

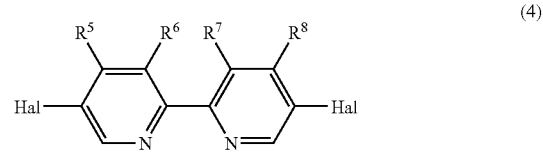
(4)

wherein Hal represents chlorine atom, bromine atom, or iodine atom, and R$^5$, R$^6$, R$^7$, and R$^8$ independently represent the same substituent as the one defined for formula (1), with a silicon compound represented by the general formula (3) of claim 3.

5. A transition metal complex containing the 2,2'-bipyridine derivative having a reactive silyl group of claim 1 as at least one ligand.

6. The transition metal complex according to claim 5 wherein the transition metal is selected from manganese, iron, ruthenium, osmium, cobalt, rhodium, iridium, nickel, palladium, platinum, and copper.

7. The transition metal complex according to claim 5 represented by the following general formula (5):

$$(X)_mM(L^1)n(L^2)_p \quad (5)$$

wherein M is a transition metal selected from manganese, iron, ruthenium, osmium, cobalt, rhodium, iridium, nickel, palladium, platinum, and copper, m is an integer of 0 to 3, X is independently selected from a halogen atom, thiocyanate group, thioisocyanate group, hydroxy group, cyano group, cyanate group, isocyanate group, and carbonyl group, n is an integer of 1 to 3, L$^1$ is a 2,2'-bipyridine derivative having a reactive silyl group represented by the general formula (1) of claim 1, p is an integer of 0 to 2, L$^2$ is a 2,2'-bipyridine derivative represented by the following general formula (6):

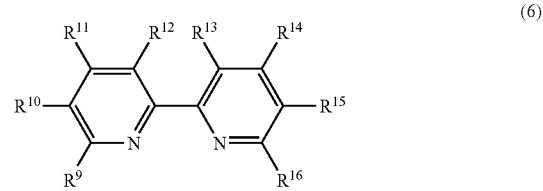
(6)

8. The 2,2'-bipyridine derivative having a reactive silyl group according to claim 1 wherein R$^3$ in the general formula (1) is vinyl group, ethoxy group or hydrogen atom and R$^4$ to R$^8$ are hydrogen atom.

9. The 2,2'-bipyridine derivative having a reactive silyl group according to claim 4 which is 5-diisopropylsilyl-2,2'-bipyridine.

10. The 2,2'-bipyridine derivative having a reactive silyl group represented by the following general formula (1'):

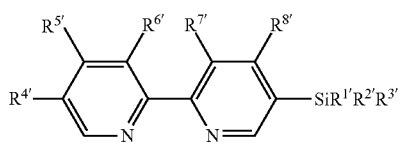

(1')

wherein $R^{1'}$ and $R^{2'}$ independently represent a substituent selected from an unsubstituted or substituted monovalent hydrocarbon group containing 1 to 10 carbon atoms, an unsubstituted or substituted organoxy group containing 1 to 10 carbon atoms, an unsubstituted or substituted acyloxy group containing 1 to 10 carbon atoms, hydroxy group, a halogen atom, hydrogen atom, mercapto group, an unsubstituted or substituted amino group, cyano group, cyanate group, isocyanate group, thiocyanate group, and isothiocyanate group; $R^{3'}$ represents cyano group, cyanate group, thiocyanate group, and isothiocyanate group; $R^{4'}$ represents a reactive silyl group represented by the formula: $R^{1'}R^{2'}R^{3'}Si$, an unsubstituted or substituted monovalent hydrocarbon group containing 1 to 10 carbon atoms, or hydrogen atom; $R^{5'}$, $R^{6'}$, $R^{7'}$, and $R^{8'}$ are independently an unsubstituted or substituted monovalent hydrocarbon group containing 1 to 10 carbon atoms or hydrogen atom.

11. The 2,2'-bipyridine derivative having a reactive silyl group according to claim 4 wherein $R^{1'}$ and $R^{2'}$ in the general formula (1') are methyl group or isopropyl group.

* * * * *